United States Patent [19]

Pilarczyk

[11] Patent Number: 4,766,542
[45] Date of Patent: Aug. 23, 1988

[54] SYSTEM AND SOFTWARE FOR PHARMACEUTICAL PRESCRIPTION COMPLIANCE

[75] Inventor: Richard R. Pilarczyk, Aurora, Ohio

[73] Assignee: General Computer Corporation, Twinsburg, Ohio

[21] Appl. No.: 928,850

[22] Filed: Nov. 7, 1986

[51] Int. Cl.⁴ ........................ G06F 15/24; G06F 15/42
[52] U.S. Cl. ..................................... 364/413; 364/401
[58] Field of Search ............... 364/400, 401, 413, 478, 364/479

Primary Examiner—Jerry Smith
Assistant Examiner—Allen MacDonald
Attorney, Agent, or Firm—Renner, Otto, Boisselle & Sklar

[57] ABSTRACT

A system for contacting customers of a pharmacy automatically to remind them that their prescriptions need to be refilled does so using a computer, memory, and automatic telephone dialing and voice synthesizing equipment. Information concerning each customer and his or her prescription is placed in a database in the memory. A schedule file which lists customer name, phone number, the drug prescribed and refill due date is created from this information. The schedule file is kept in chronological order by refill due date. At selected times, customers whose prescriptions are due to be refilled within selected time periods are automatically contacted by the computer using the automatic telephone dialer. When the telephone is answered, the voice synthesizer identifies the customer by name, the prescribed drug and prescription number. The voice synthesizer then reminds the customer that the prescription is due to be refilled if the medication was taken as prescribed. The system generates various reports for the pharmacist concerning its automatic activities.

15 Claims, 3 Drawing Sheets

SYSTEM AND SOFTWARE FOR PHARMACEUTICAL PRESCRIPTION COMPLIANCE

FIELD OF THE INVENTION

The present invention relates generally to automated prescription drug refill systems and methods for pharmacies and specifically to hardware and software used in a pharmacy to automatically contact customers whose prescriptions need to be refilled.

BACKGROUND OF THE INVENTION

Many drug prescriptions written by physicians require or permit an extended regimen which is necessary for effective patient care. For many prescribed drugs, however, the patient may not obtain the full prescribed number of doses of the drug when he visits the pharmacy. There are many reasons for this. For example, the drug may be perishable. The drug may be expensive, and the patient may prefer to purchase it in smaller quantities in order to spread out the cost. Finally, many drugs such as heart medications are taken over an extended period of time, and it would not be practical to dispense a large number of doses of the drug. For these reasons, among others, prescriptions are often written with a certain number of refills. When the patient runs out of the prescribed drug, he should return to a pharmacy to have his prescription refilled.

Many patients do not fully comply with the specified regimen of taking prescribed drugs. They may, for example, fail to take the drug four times a day when that is prescribed. They may also fail to get a drug prescription refilled when they run out of the medication. The cost to the patient and to society for such negligence is great. Often, the result of failing to take the prescribed medication is a worsened disease with resultant hospitalization. The hospitalization is inevitably more expensive than the cost of the medication which, had it been taken as scheduled, might have prevented the illness.

In addition to the broad public health reasons noted above, pharmacists are concerned about having prescriptions refilled from a simple business point of view. Customers who come into a drugstore to have a prescription refilled are likely also to purchase other items available at a drugstore. Therefore, a method or device which can increase the number of customers returning to have prescriptions refilled is likely also to benefit sales of collateral items.

SUMMARY OF THE INVENTION

The present invention provides a computerized system for contacting patients whose prescriptions are due to be refilled. The hardware and software automatically telephones each customer whose prescription needs refilling. The contact is made with a computer driven voice synthesizer which delivers a personalized message identifying the customer, the drug in question and the prescription number. All of this is done without contemporaneous assistance from the pharmacist who is therefore free to attend to other duties.

The telephone dialer and voice synthesizer read data from a schedule file. The schedule file lists all prescriptions issued by the pharmacy according to the date when the customer (patient) should require more medication. The schedule file is updated regularly based on prescription refill activity at the pharmacy. The system takes as input customer identification information, the drug prescribed, the dose prescribed, and the number of doses given to the customer. From this information it calculates the day the customer's supply of the prescribed drug should run out. This date is the date entered in the schedule file.

The pharmacist may periodically review the contents of the schedule file to note those customers whom he does not want to contact concerning refills. The pharmacist may choose not to contact a customer because the customer is clearly a transient, or for some other reason. All other customers on the schedule file are identified as ones to be called.

After those customers whom the pharmacist wishes to contact have been flagged on the schedule file, the pharmacist selects that group of customers from the schedule file whose prescriptions have certain refill dates. For example, the pharmacist may choose to contact all customers whose prescriptions will expire during the next two weeks. Alternatively, he may choose to contact all patients whose prescriptions expired in the previous two weeks and who have not refilled their prescriptions. After this choice has been made, the automatic customer contacting system takes over. The device automatically dials each customer's designated phone number, identifies the person whose prescription needs refilling, the prescription to be filled and its refill date. The system then asks the customer to confirm that the message has been received. This process is repeated by the automatic telephoning equipment until each person on the schedule file has either been reached, or the system has made a number, e.g., at least four, unsuccessful attempts to contact the customer.

The system also provides printed reports to the pharmacist on its activities including with respect to each prescription whether it was refilled early, on time, or late. Whether, if the refill was requested, it was not picked up, or whether it was not requested to be refilled at all. With respect to each of these categories, reports from the system will tell the pharmacist whether the customer has been contacted by the system, whether the customer was one whom the system attempted to contact and was unable to contact or whether the customer was one which the pharmacist had pared out of the schedule file as one the pharmacist did not wish to contact.

Briefly, then, the invention relates to an apparatus for automatically contacting patients regarding prescription drug information, including a memory device for storing information concerning patients, prescription drugs, prescription refill requirements, and telephone numbers of patients. The apparatus also includes a telephone dialer for dialing the telephone numbers of the respective patients, a voice synthesizer for communicating prescription drug refill information, a computer for interacting with and controlling operation of the memory device, the telephone dialer, and the communicating device, and a program control for controlling the computer to cause the telephone dialer automatically to dial telephone numbers of patients so that the communicating device can communicate prescription drug refill information based on information stored in the memory device.

Another aspect of the invention provides a method for automatically contacting patients regarding prescription drug information. The method includes storing in a memory device information concerning patients, prescription drugs, prescription refill requirements, and telephone numbers of respective patients, using a computer to review the information stored in the memory device and detecting a prescription that requires refilling, and using automatic telephone dialing equipment to automatically dial the telephone number of a patient whose detected prescription requires refilling for communicating information that the prescription requires refilling.

To the accomplishment of the foregoing and related ends, the invention, then, comprises the features hereinafter fully described in the specification and particularly pointed out in the claims, the following description and the annexed drawings setting forth in detail a certain illustrative embodiment of the invention, this being indicative, however, of but one of the various ways in which the principles of the invention may be employed.

DESCRIPTION OF PREFERRED EMBODIMENT

Figure 1:
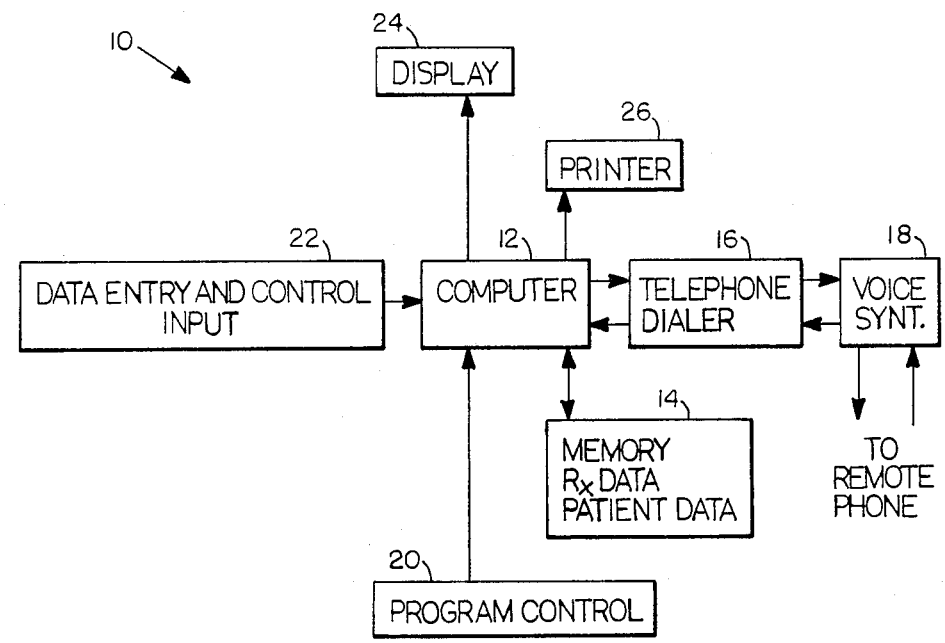
FIG. 1 is a schematic block diagram of the system for pharmaceutical compliance in accordance with the invention.

Referring in detail to the drawings, wherein like reference numerals designate like parts in the several figures, and initially to FIG. 1, a system for pharmaceutical prescription compliance in accordance with the preferred embodiment and best mode of the present invention is designated 10. The system 10 includes a computer 12, preferably a general purpose computer. The computer 12 may be a minicomputer, a microcomputer, or a mainframe computer, although in the preferred embodiment, the computer is a minicomputer. Associated with the computer 12 as part of the system 10 is a memory 14, which stores information, for example in the form of a data base. Such information may include, for example, the names of pharmacy customers, the telephone numbers and possibly also the addresses of the patients, prescription drug information, namely what prescription drugs have been prescribed for the respective patients, date information concerning when a prescription should be refilled, and possibly additional information, as well, as is described further below. The system 10 further includes an automatic telephone dialer 16, which is controlled by the computer 12 to dial the telephone numbers of respective patients when the computer detects information, for example that stored in the memory 14, indicating that a prescription should be refilled. Associated with the telephone dialer 16 is a voice synthesizer 18 able to provide oral information when a telephone connection is made so that the need to refill the prescription is communicated. Although the telephone dialer 16 and voice synthesizer 18 are responsive to effect automatic telephone number dialing and audible, oral output, respectively, under control of the computer 12, such dialer 16 and synthesizer 18 also preferably are coupled back to the computer to provide information indicating that a telephone connection has been made and that an acknowledgement of the making of such connection has been received from the remote called telephone. Such information can be stored and subsequently used or furnished to a user of the system 10.

A program control designated 20 is coupled to the computer 12 and may in fact be a part of the computer, either in ROM, RAM or may be a disc drive or other mass storage device to provide computer program controlled operation of the computer 12 and the equipment associated therewith. Thus, the actual operation of the system 10 is under the computer program control guidance of the program control 20, and the method of the present invention also is guided thereby, as will be described in greater detail below.

A data entry and control input 22 is coupled to the computer 12, and may be, for example, a keyboard through which an operator can control operation of the system 10 or can input data to the system 10. The data entry and control input 22 also may include a coupling mechanism to other means, such as another computer or the like, to receive input information, such as the names of patients, prescription drug information, prescription refill information, and the like, which is to be stored in the memory 14.

A display 24, such as a conventional computer monitor, is coupled to the computer 12, and a printer 26, such as a conventional dot matrix printer or other printer, also is coupled to the computer 12. The display 24 may be used to display information to the operator indicating the current operation or operations being carried out by the system 10, indicating information being input by the operator through the data entry and control input 22, for example, and for various other purposes, as may be desired. The printer can be used to provide hard copy output information concerning the names of patients, the prescription drugs used by such patients, prescription refill dates, and/or other information, as may be desired.

The computer 12 may be, for example, an NEC Astra minicomputer Model 2XX or Model 3XX. The former is a 16-bit computer while the latter is a 32-bit computer with between 512K and 6 megabytes of main memory, depending on configuration desired by the user. The memory 14 may be, for example, a conventional hard disc or floppy disc drive or other mass storage device for storing information received from the computer and communicating the information back to the computer 12. The automatic telephone dialer 16 and the voice synthesizer 18 may be separate devices or, according to the preferred embodiment, may be an automatic telephone dialer and speech synthesizer combination device sold under the brand name CALL TEXT 5050 marketed by Speech Plus of Mountain View, Calif. Although preferred equipment is mentioned, it will be appreciated that other equipment or apparatus may be used in accordance with the present invention, as will be apparent to those having ordinary skill in the art.

The preferred embodiment of the present invention utilizes a data base stored in memory 14 which includes specific information on a pharmacy's daily prescription activity. For example, the data base includes each customer's name, address, and phone number, the drug prescribed for the customer and the prescription number, the prescribing doctor, the doctor's address, the doctor's phone number, and the doctor's Drug Enforcement Agency registration number. The file also includes the amount of the drug dispensed, the prescribed frequency with which the patient is supposed to take the drug, the number of days the dispensed amount should last if taken as prescribed (hereinafter, days supply) the date of filing the prescription, and the number of refills prescribed by the doctor. This data base may be maintained manually, but preferably it is maintained automatically by computer software sold by The General Computer Corporation of Twinsburg, Ohio, under the trademark THE SOLUTION and which is intended to run on the computer 12. Preferably the computer 12 in the system 10 is the same computer as that used for running THE SOLUTION computer software so that both THE SOLUTION software and the system of the present invention are fully compatible and useful essentially in a single automated system that provides both the functions of THE SOLUTION software and the pharmaceutical prescription compliance method of the present invention.

Figure 2:
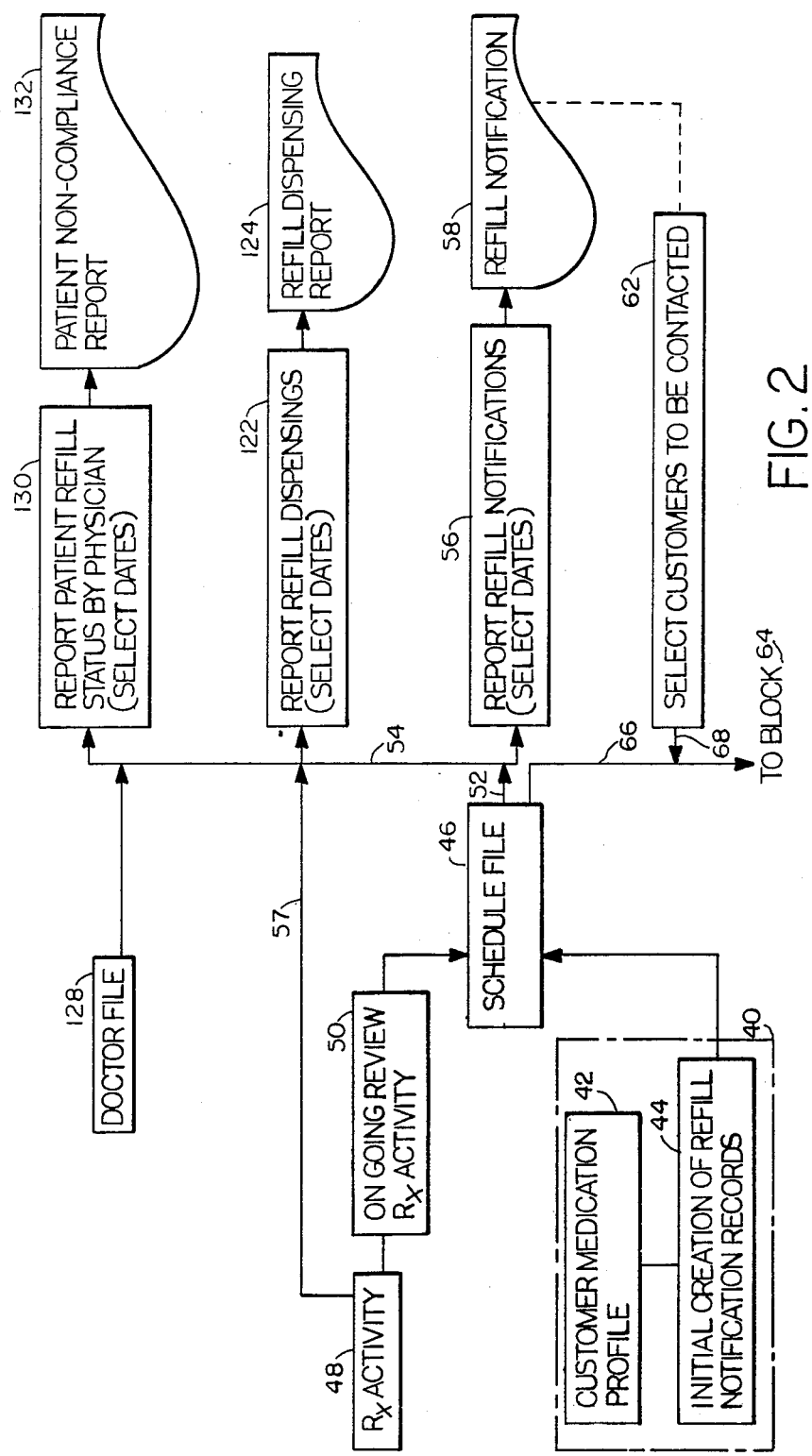
FIGS. 2 and 3 are a representative flow chart of procedures and steps followed in operation of the system of FIG. 1 in accordance with the method of the invention.
Figure 3:
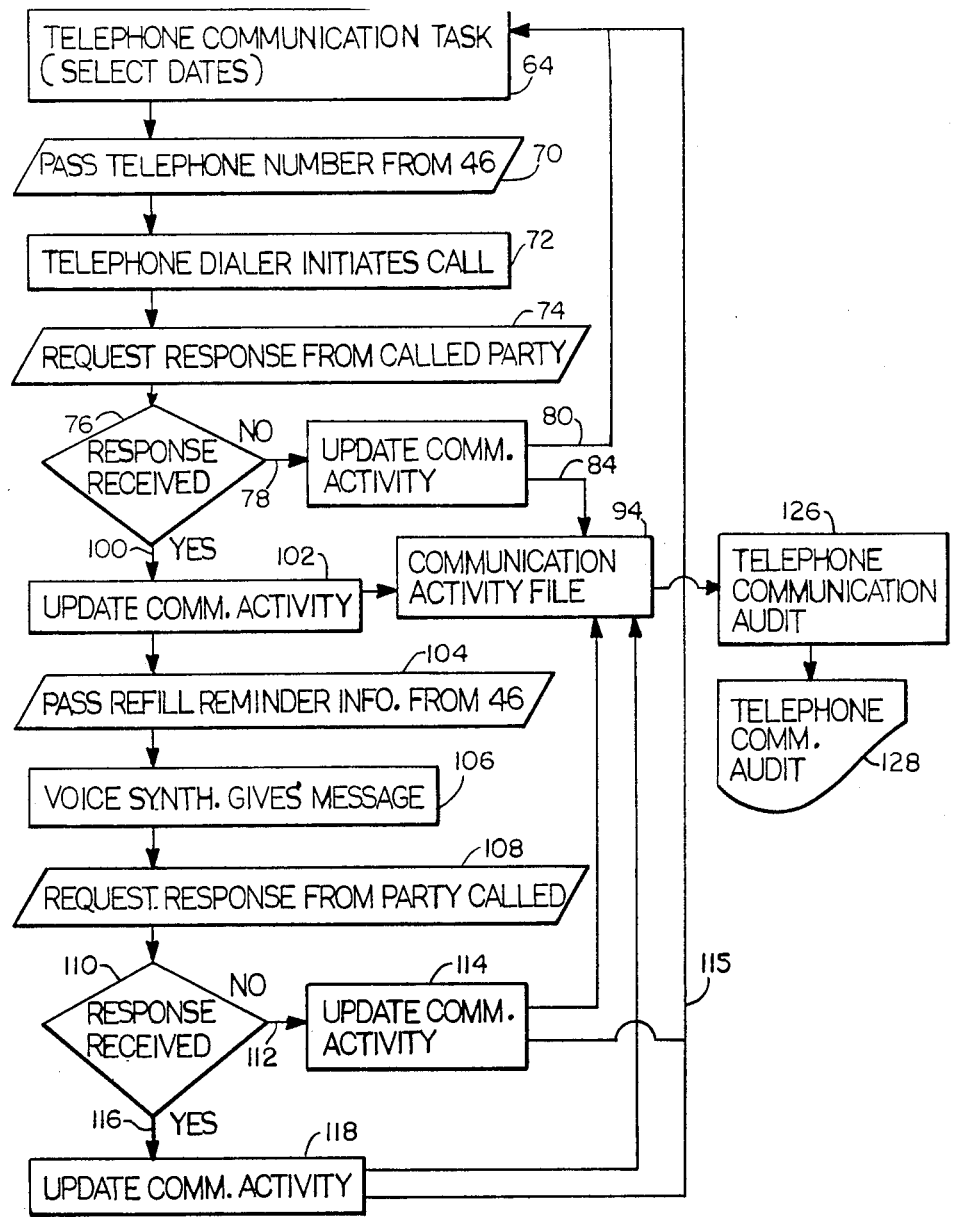

Turning now to FIGS. 2 and 3 of the drawings, the computer program flow chart and method steps of operation of the present invention are depicted by various blocks and steps identified therein. These will be described in further detail below.

Initially referring to FIG. 2, there is disclosed the initialization/file creation portion of the program, generally designated at 40. The portion 40 includes a block 42 representing the input or receipt of data concerning patient medication profile information and a block 44 at which there is an initial creation of prescription drug refill notification records. The patient medication profile information at block 42 may be received, for example, from existing records in another computer, another memory, or from another apparatus, as was mentioned above in the description of the data entry and control input 22 of FIG. 1, to provide the information intended for storage in the memory 14 (FIG. 1). At block 44 the information received at block 42 is used to create refill notification records that are delivered for storage in the memory 14.

The refill notification records from block 44 are rearranged into an initial schedule file at block 46. This schedule file contains all prescriptions the pharmacy can expect to refill, and the information necessary to place a reminder phone call, i.e., customer name, phone number, prescription number and medication name. The schedule file contains information on a date basis representing when a prescription refill should be required and can be relied on by the computer 12 detecting respective records based on date information, for example, to effect the communication function of the system 10 by using the telephone dialer 16 and voice synthesizer 18.

Creation of the schedule file 46 may be effected by the computer 12 operating on the refill notification records obtained in block 44 so that such records are stored in the memory 14 chronologically for the mentioned communication function. The actual refill notification records developed in block 44 may or may not be stored in the memory 14; it is important, though, that the schedule file developed in block 46 is stored or that means are provided to detect from the refill notification records when it is appropriate to communicate refill information to a patient.

Also in FIG. 2 is block 48 representing prescription activity inputs, which may be, for example, effected by operation of the data entry and control input 22 by the pharmacist when a prescription is prepared and delivered to a customer. In this regard, the pharmacist enters all the information required by the data base described above.

Typically the prescription activity information at block 48 would be entered as a prescription is filled and delivered, but it could be done on a daily basis, or on some other periodic basis, as may be desired. Blocks 42 and 44 represent an initial start-up of the system 10, whereby the system 10 receives complete information of all existing records kept in the pharmacy, but block 48 represents a daily or other short term periodic entry of information on a relatively timely basis. Thus were the system 10 directly associated with THE SOLUTION software system, block 48 would represent acquisition of the data stored in THE SOLUTION software system concerning the daily prescription drug activity at a pharmacy.

At block 50 an ongoing review of prescription activity is carried out prior to sending the information to the schedule file. At block 50 all prescriptions without refills which were part of the pharmacy's daily activity are filtered so that data concerning them is not sent to the schedule file. Also as noted above, the schedule file (block 46) includes only the information necessary for making a reminder phone call, while the daily prescription activity file includes all the data required by the data base described above. Specifically the data base stored in memory 14 includes additional information beyond that in the schedule file on the number of refills, the date of last refill, the prescribing doctor and his D.E.A. number, etc.

The ongoing review of prescription activity at block 50 is initiated by the pharmacist. In the event that the system 10 of the present invention is used in connection with THE SOLUTION software, at the end of a business day or at some other time when the memory 14 is available and not being used by the subroutines in THE SOLUTION software, the pharmacist initiates the review activity of block 50. The data reflecting the daily (or some other time period) prescription activity from the memory 14 are then culled and the more limited data required by the schedule file are forwarded to the schedule file. In this way the schedule file is kept current. Of course, if the system 10 is not used in conjunction with THE SOLUTION software, the culling of pharmacy activity may be accomplished in some other way, including possibly manually through use of the data entry keyboard 22.

Block 50 also calculates the refill due date based on the daily prescription activity. Specifically from the number of refills prescribed, the date of the last refill dispensed, the days supply dispensed at that time, the number of refills remaining and an internal calendar, a refill due date is calculated. All records are stored in the schedule file based on this calculated refill due date. When the records indicate that there are no refills remaining, the prescription record is automatically culled and not forwarded to the schedule file 46.

The information contained in the schedule file 46, for example, stored in the memory 14, is delivered via lines 52 and 54 to a report refill notifications block 56. In addition data from the prescription activity file 48 and associated with each record in the schedule file is sent to block 56 via lines 54 and 57. At block 56 the pharmacist then selects the time span over which he wishes to review the schedule file for customers he wants to contact. The computer 12 then detects chronologically the prescriptions to be refilled. For example, if the schedule file 46 in memory 14 contained a number of records that should be called up for prescription refill notifications on a given day or within the selected time span, the computer 12 would detect them, select them and would prepare a report at block 56 of those records. The computer 12 would then draw additional information from the data base stored in memory 14 to complete the refill notification report.

The schedule file includes the customer's name, phone number, prescription refill due date, prescription number and the drug name. To complete the refill notification report the computer adds from the memory-stored data base the customer's address, the amount, e.g., number of capsules, to be dispensed with each refill, the number of days supply in each refill, the schedule on which the customer was told to take the drug, the date of last refill and the number of days supply of the last refill. The refill notification report lists every prescription to be refilled in the time period selected by the pharmacist together with the above information as to each.

The refill notification report 58 is printed on paper by printer 26 so that the pharmacist can review it and remove any customers he does not want to contact. At block 62 the pharmacist flags those records that are to be passed through to a telephone communication task block 64. The flags representing customers to be called over the selected time period are sent to the schedule file 46 which is then ready to begin the telephone communication task at block 64.

At block 64 (FIG. 3) the telephone communication task is to be undertaken. To do so the pharmacist must select the time span of prescription refill due dates to be notified. Usually this will be the same time span selected for the Refill Notification Report (block 56, FIG. 2) but a shorter time period could be selected. Once the time period of due dates to be covered is selected, the telephoning task is automatically undertaken. At block 64 (FIG. 3) each record that is to be communicated is called up sequentially and the steps described further below for telephoning will be carried out for each selected record.

At block 70 the telephone number stored in the given record of the schedule file is obtained and is sent to the telephone dialer and voice synthesizer 16, 18. At block 72 the dialer and synthesizer are activated to initiate the telephone call. As soon as the call is initiated at block 72, the voice synthesizer 18 is activated to deliver a message repeatedly without detecting whether or not the telephone call has in fact been answered. The message may be, for example, "Hello, this is your pharmacy calling, if you have answered the phone, please acknowledge by pressing the number 2 on your telephone key pad." This message is repeated for a prescribed period of time or until receipt of a tone representing the pressing of the digit 2 on the telephone keypad of a Touch Tone telephone.

Block 74 determines whether the digit 2 on the telephone key pad has been pressed. Such detection can be effected using conventional equipment and, in particular, the CALL TEXT 5050 speech synthesizer has the capability of detecting such a tone. At block 76 an inquiry is made to determine whether or not the digit 2 has been pressed. If not, then line 78 is followed to block 80 for updating an activity record, described further below, and to schedule the record for a re-try, i.e., calling again, at a future time. Thereafter, at line 82, the program returns to block 64 to continue with the telephone communication task. Since the telephone call was unanswered, at the telephone communication task block 64 the record would be placed at the end of the stack of records intended for being called in a given time frame.

The communication activity file update is effected at line 84. Through line 84 the information concerning the failure to complete the call is stored in the communication activity file at block 94.

If a number 2 pressed, a response received signal is detected at block 76, then following line 100 to block 102 the activity file is updated at block 94 to confirm that a call has in fact been completed.

Thereafter, at block 104 the refill reminder information is obtained from the schedule file and passed to the voice synthesizer 18, and at block 106, the voice synthesizer 18 actually communicates the refill reminder information to the party on the telephone.

At block 108 the voice synthesizer 18 requests the answering party to press the number 2 again (or other number or key) to acknowledge that the message in fact has been received and understood. Then at block 110 an inquiry is made to see whether or not such acknowledgement was received from block 108. If negative, then following line 112 to block 114 the activity record is updated to indicate that the latter acknowledgement was not received, and the flow chart returns via line 115 back to the telephone communication task block 64 where the record again is placed in the stack for re-trying in the future. On the other hand, if the acknowledgement was received at block 110, then following line 116 to block 118, the activity record is updated, and thereafter the flow chart returns via line 115 to the telephone communication task 64. However, in this case, since the call was completed, the record is identified as one that does not have to be re-called in the immediate session.

To recapitulate briefly, the system of the present invention audits the daily activity of the pharmacy either by making an inquiry in THE SOLUTION software or by manual entry of the data into the system. The data is used to create a schedule file 46 (FIG. 2). The schedule file lists all the prescriptions according to the date when they will need to be refilled, determined by consulting the daily activity input for the date of filling of the prescription, the prescribed schedule, and the amount of the drug dispensed. From this the software calculates the refill date of each prescription. Further, in creating the schedule file, the software consults the data base for the number of refills and number of doses remaining on the prescription. If no refills or doses are remaining, then the prescription is not placed on the schedule file.

Of course, on initial installation the schedule file will have to be created from a log of all of the pharmacy's past activities reaching back a reasonable period of time. Thereafter, the schedule file merely requires updating based on each day's activity.

Once the schedule file is created the software prints out a hard copy of the customers to be contacted, the Refill Notification Report (block 58, FIG. 3). The pharmacist may choose whether this hard copy lists the entire schedule file or only those customers whose prescriptions expire within a certain time period. Regardless of which choice is made, the pharmacist then has an opportunity (block 62) to select those customers on the schedule file whom he wishes and does not wish to contact. There are numerous reasons why this might be done. For example, the customer may have been a transient, or the pharmacist may have learned that the customer is no longer in the area or has died. It may be that the pharmacist knows the customer personally and wants to make a personal phone call to the customer.

When the pharmacist wishes to have the customers contacted automatically, he initiates the telephone communication task, block 64. This involves selecting from the schedule file the prescription refill dates which the pharmacist wishes to contact. It may be, for example, that the pharmacist wishes to contact customers whose prescriptions are due to be refilled within the next two weeks. Conversely, he might choose to contact only those customers whose prescriptions should have been refilled in the past two weeks. In any event, the pharmacist must select the time span from the edited schedule file covered by the prescription refill dates of the customers he wishes to contact. Once this is done, the automatic calling device takes over.

The automatic calling device preferred is sold under the brand name CALL TEXT 5050 marketed by Speech Plus of Mountain View, Calif. It has an RS232 peripheral communication system which enables it to communicate with the NEC Astra minicomputer which in the preferred embodiment contains the data base from which the schedule file is created. CALL TEXT has the ability to convert English text messages into speech. It also has automatic dialing facilities and may be connected to an outside telephone line through a standard RJ11C modular telephone jack.

The system's software consults the first entry in the schedule file to be called and determines the phone number to be dialed, block 70. The automatic dialer then initiates the call, block 72, and begins, without waiting for the phone to be answered, to announce itself. Thus it may say "This is your pharmacy calling; if you have answered the phone, please press 2", as indicated at block 74. If no response is received within 30 seconds, the system proceeds to block 80, makes a record of the failure to reach the customer and returns to the telephone communication task, block 64, which consults the edited schedule file at block 62 for the next scheduled call.

If the customer responds by pressing 2, as requested by the automatic dialing device at block 74, the software proceeds to block 102, where the fact that the call was received is recorded. The software then refers, at block 104, to the schedule file for the refill reminder information. This information includes the patient's name, the prescription number, and the name of the drug. The automatic dialer/voice synthesizer device then gives a refill message which may be along the following lines:

"This is the MEDMINDER service from Jones Drug on Center Street. The prescription for Mr. Smith for Tagamet, 100 milligrams is due for refill if it has been taken as prescribed. If you wish to refill prescription number 123456 please contact the pharmacy at 123-4567."

Once the refill reminder message has been given, block 106, the system asks for a further response from the message receiver as shown at block 108. This response, if received, confirms that the message was delivered in full. On the other hand, if this second response from the recipient is not received, the system considers that the call was not made. In either event, as indicated at blocks 118 and 114, respectively, a record is made of the event. Thereafter, the software returns to the telephone communication block 64 which consults the schedule file, block 46, for the next scheduled call.

The system will proceed through the loop defined by blocks 64-118 until all customers on the selected portion of the schedule file have been contacted or until four attempts have been made to reach the customer.

The system is designed to produce records of its activity so that the pharmacist can appraise its effectiveness. Blocks 80, 102, 114 and 118 (FIG. 3) send entries into the communication activity file, block 94. The system will provide reports to the pharmacist of the pharmacy's refill dispensing activity over a selected period of time. At block 122 (FIG. 2) the pharmacist may choose to have a report of refills dispensed over a selected time period. The computer 12 creates the Refill Dispensing Report 124 by collating data from the complete schedule file, block 46, together with additional data from the complete data base corresponding to each record in the schedule file. The Refill Dispensing Report includes the identity of each customer whose prescription required refilling during the selected period and the prescription number. The report also includes the drug prescribed, the number of doses per refill, the date the refill was due to be refilled, whether it was refilled, and if so whether it was refilled on time, early or late. Although this information is theoretically available to the pharmacist without the system of the present invention, most pharmacists do not have the time to collate it manually.

The Refill Dispensing Report 124 also includes a summary of the effectiveness of the automated customer contacting system. The report lists the results for three categories of customers: those the pharmacist chose and successfully contacted with the automated system described, those he chose to contact but whom the system was unable to reach, and those he chose not to contact. With respect to each of these categories the summary lists the number who refilled early, i.e. more than five days before the refill due date; the number who refilled on time, i.e., within five days of the due date; the number who refilled late, i.e. more than five days after the due date; the number who requested a prescription refill but did not pick it up; and the number who did not get their prescriptions refilled.

A second report available from the system is a Phone Call Audit. At block 126 (FIG. 3) the pharmacist may select the time period he wishes the audit to cover. The computer 12 then consults the schedule file 46 and communication activity file 94. The Phone Call Audit Report 128 lists each phone call made by customer name, the prescription in connection with which the phone call was made, the date and time of the call and whether it was completed or not. This report provides a permanent record of what calls were made and when in case of any later dispute.

An additional capability of the present system is illustrated in FIG. 2. The pharmacist at block 130 may request a Patient Noncompliance Report 132. He must again select a time span to be covered by the report. The computer 12 then collates data from the schedule file, the prescription activity file and from a Doctor File 128. The latter contains names and addresses of various doctors serviced by the pharmacy and is kept automatically by THE SOLUTION software, if the latter is used. Otherwise this data must be input manually through keyboard 22 or obtained from some other data base. The Patient Noncompliance Report 132 is a separate report to each doctor detailing which of his patients refilled prescriptions early, on time, late, or not at all. This information might be helpful to the doctor in treating the patient.

Several additions and modifications to the present system are also contemplated. For example, some customers may need to be notified each time they are to take a drug. There is no reason why the schedule file cannot contain a clock and instructions to dial a particular patient at a particular time of day, or even at multiple times on a single day. Further, where the prescribed drug has a name which is particularly difficult for the voice synthesizer to pronounce, further identification of the drug in the telephone message could be included. For example the drug could be identified as "the blue and white tablet". In the block 110, additional questions could be asked. For example, the customer could be told that if he wanted a prescription refilled he should indicate by pressing some particular number on his Touch Tone phone, or if he wanted the pharmacist to call him he should push another number.

What is claimed is:

1. An apparatus for automatically contacting customers of a pharmacist to remind them of the need to have a prescription refilled, said apparatus comprising
   memory means for storing information concerning each customer's name, phone number, the medication prescribed for the customer, the prescribed schedule for taking the drug, the number of doses to be dispensed, the number of refills prescribed and dispensed and the date on which the prescription will require refilling if each dose is taken on schedule,
   telephone dialer means for dialing telephone numbers,
   communicating means for communicating prescription drug refill information along a telephone connection made by the telephone dialer means,
   computer means for interacting with and controlling operation of the memory means, telephone dialer means and communicating means, and
   program control means for controlling said computer means to dial the telephone number of customers to communicate prescription drug refill information based on information stored in the memory means.

2. The apparatus of claim 1 including means for determining whether the telephone called has been answered and for transmitting a first response to the computer if the telephone has been answered and a second response to the computer if it has not been answered.

3. The apparatus of claim 1 further including means within said program control means, for deriving the date on which a prescription will require refilling if each dose is taken on schedule from the prescribed schedule for taking the drugs, and the number of doses dispensed.

4. The apparatus of claim 3 including data entry means for entering information as the pharmacist is dispensing a prescription, said data entry means being connected with said computer means.

5. The apparatus of claim 4 including schedule means for storing the information in the memory means in chronological order according to the date on which each prescription will require refilling if each dose is taken on schedule.

6. The apparatus of claim 5 including updating means for updating the information stored in said schedule means in response to information entered in said data entry means.

7. A method for automatically contacting customers of a pharmacist to remind them of the need to have a prescription refilled, said method comprising the steps of
   receiving information concerning each customer's name, phone number, the medication prescribed, the schedule prescribed for taking the medication, the number of doses to be dispensed and the number of refills prescribed and dispensed,
   computing from the information received a refill due date corresponding to the day on which each prescription will require refilling,
   storing at least a portion of the information received together with the associated refill due date in chronological order,
   using a computer receiving the stored information and refill due date to detect prescriptions requiring refill, and
   using automatic telephone dialing means for automatically dialing the telephone number of a customer whose prescription requires refilling for communicating the information that the prescription requires refilling to the customer.

8. The method of claim 7 wherein the step of using a computer includes the step of selecting a range of refill due dates and identifying any prescription having a refill due date within the selected range as one requiring refill.

9. The method of claim 8 including generating in machine readable form the information received at approximately the same time as the pharmacist fills the prescription to which the information relates.

10. The method of claim 8 further including the step of requesting the person receiving a telephone call from the automatic telephone dialing means to indicate that the call has been received.

11. The method of claim 10 further including the step of transmitting information concerning the prescription requiring refill upon receipt of the indication that the call has been received.

12. The method of claim 11 wherein the step of transmitting information includes the steps of recalling the stored information associated with the prescription requiring refill and using a voice synthesizer to convert the information so recalled to an oral message and delivering the same.

13. The method of claim 12 including the step of requesting an acknowledgement that the message has been received after the message has been delivered.

14. The method of claim 10 including the step of determining whether an acknowledgement of the telephone call has been received and, if not, re-trying the telephone call at a later time.

15. The method of claim 8 including the step of producing a listing of each customer having a prescription requiring refill, the customer's phone number, the prescribed drug, the amount prescribed, the number of days of supply per refill, the schedule prescribed for taking the drug, the date the last refill was dispensed and the number of days' supply dispensed at that time, and selecting from the listing those customers to be automatically contacted.

* * * * *